(12) United States Patent
Dvoskin

(10) Patent No.: US 6,941,653 B2
(45) Date of Patent: Sep. 13, 2005

(54) METHOD AND APPARATUS FOR FORMING A REFRACTORY LINING IN A CORELESS FURNACE

(75) Inventor: Leonid Dvoskin, Milwaukee, WI (US)

(73) Assignee: International Engine Intellectual Property Company, LLC, Warrenville, IL (US)

( * ) Notice: Subject to any disclaimer, the term of this patent is extended or adjusted under 35 U.S.C. 154(b) by 132 days.

(21) Appl. No.: 10/620,097

(22) Filed: Jul. 15, 2003

(65) Prior Publication Data
US 2005/0015985 A1 Jan. 27, 2005

(51) Int. Cl.$^7$ .............................................. B21D 47/00
(52) U.S. Cl. .................... 29/897.1; 29/407.09; 29/406; 266/281
(58) Field of Search ....................... 29/890.051, 890.03, 29/897.1, 897.3, 897.34, 402.01, 402.08, 402.09, 406, 407.09, 407.1, 526.2, 527.1, 821, 271; 266/281, 280

(56) References Cited
U.S. PATENT DOCUMENTS

| | | | |
|---|---|---|---|
| 4,251,063 A | * | 2/1981 | Goldberg et al. ........... 266/281 |
| 4,253,646 A | * | 3/1981 | Goto et al. .................. 266/281 |
| 4,570,909 A | * | 2/1986 | Hiroki et al. ............... 266/281 |
| 4,690,327 A | | 9/1987 | Takai et al. |

\* cited by examiner

Primary Examiner—John C. Hong
(74) Attorney, Agent, or Firm—Susan L. Lukasik; Dennis Kelly Sullivan; Jeffrey P. Calfa

(57) ABSTRACT

A refractory lining is formed in a furnace by providing a carrier for a lining form which has dimensions that provide a uniform space for the introduction of refractory material when the lining form is concentrically located within the furnace. The carrier concentrically engages and is attached to the lining form, and includes a portion that engages the furnace and locates the carrier and the lining form, when attached, concentrically within the furnace to provide a uniform space therebetween. The carrier can also have an upper surface that slopes downwardly from adjacent its center to its periphery to convey particulate refractory material poured onto the surface into the space between the lining form and the furnace. Further, a fixture is provided to hold the lining form concentric while the particulate refractory material is compacted by vibration.

18 Claims, 5 Drawing Sheets

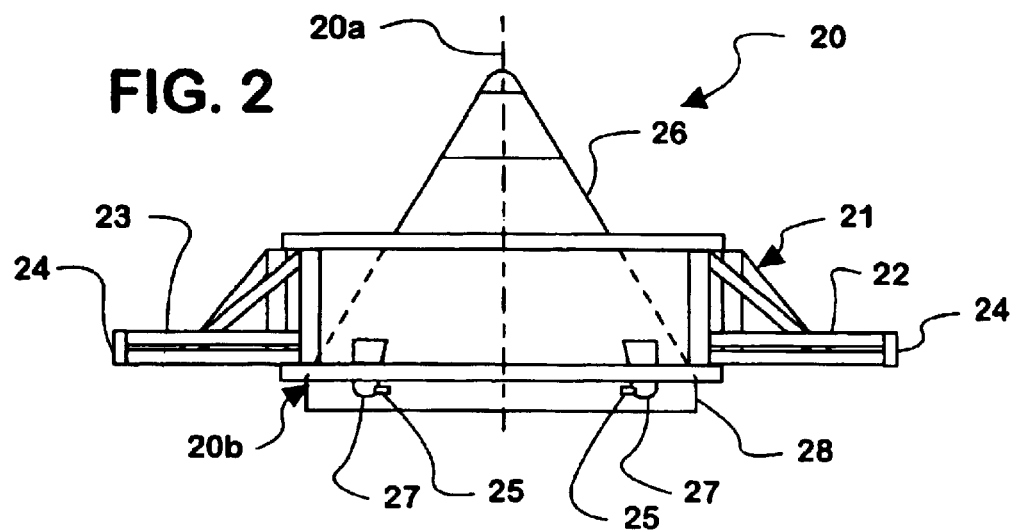
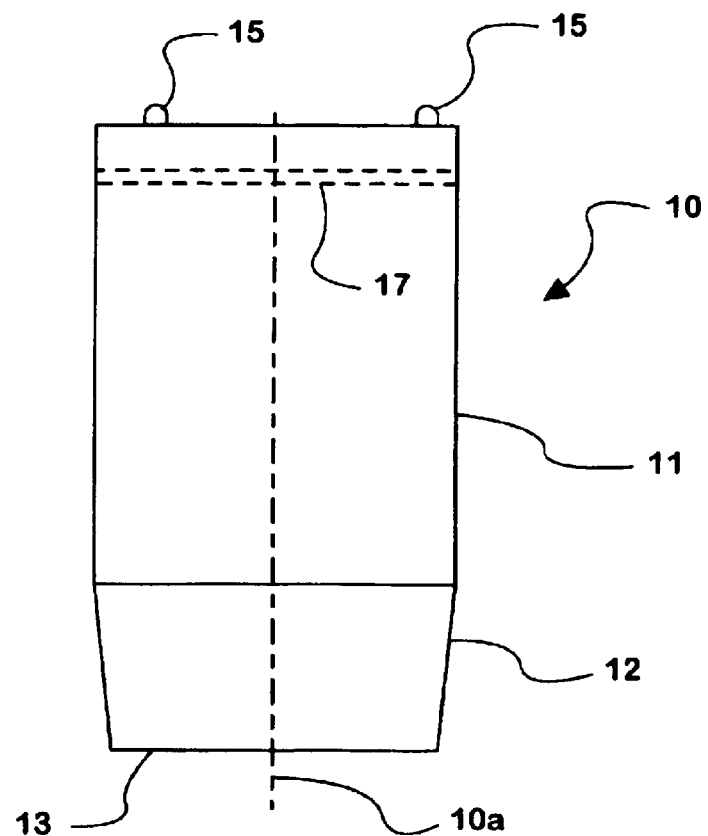

METHOD AND APPARATUS FOR FORMING A REFRACTORY LINING IN A CORELESS FURNACE

FIELD OF THE INVENTION

This invention relates to a method of forming a uniform lining of refractory material within the interior of a coreless furnace, and to apparatus therefor.

BACKGROUND OF THE INVENTION

In order to maintain furnaces in proper operating condition for preparing molten metal for casting operations, the refractory insulative lining of the furnace must be replaced about every eight weeks. In order to replace the lining, the furnace must be shut down and allowed to cool, and the existing lining must be removed, exposing the structural walls of the furnace. Following removal of the worn lining, the replacement process has, in the past, generally included the steps of 1) lowering a lining form into the furnace to form a refractory lining of uniform thickness; 2) aligning the lining form within the furnace to provide a uniform space between the exterior of the lining form and the interior of the furnace; 3) wedging the lining form, after it has been aligned, to maintain it in the aligned position; 4) pouring the refractory lining material into the space between the lining form and the furnace wall; 5) holding the lining form motionless relative to the furnace wall while compacting the refractory material with a vibrator; and 6) gradually heating the lining form to harden the new refractory lining.

In the past, there have been no fixtures to assist in the accomplishment of steps 1–5 above, and the work was conducted manually by skilled workmen, and satisfactory completion was very time consuming and required great skill and attention. It is very important for reliable operation of the furnace that the lining form be accurately aligned with the furnace to obtain a uniform layer of refractory material at the furnace wall, and it is likewise important that the lining form be held motionless in its concentric alignment with the furnace while the refractory material is being compacted.

In the past, steps 1–3 were performed as follows:

a lining form was lowered into the furnace with an overhead crane;

a plumb-bob bar was placed over the lining form into two furnace alignment holes;

a worker had to climb down into the interior of the lining form, using a ladder, and take directional measurements of the space between the lining form and the furnace wall;

the crane operator had to use the directional measurements received from the worker to manipulate the overhead crane to locate the form in an assumed concentric position.

The steps of measurement and relocation had to be repeated again and again until the lining form was positioned so that the space between the lining form and the interior furnace was uniform within one quarter of an inch.

Following the completion of steps 1–3, steps 4 and 5 were performed as follows the lining form had to be wedged into the aligned position by workers without destroying the alignment;

when the lining form was wedged into position within the furnace, the overhead crane was used to pour particulate refractory material into the relatively narrow space between the lining form and the furnace wall;

after the space between the lining form and furnace was filled with the particulate refractory material, clamping bars were manually installed on top of the form in an attempt to hold the lining form motionless while the refractory material was being compacted with vibrators.

Finally, the lining form was heated from within with a gas torch to harden the new lining and complete the process.

Because of the relatively narrow space between the lining form and the furnace wall, and the difficulty of accurately directing the particulate refractory material into the space, the pouring operation was restricted to the use of bags of refractory material that were no larger than 100-pound capacity.

This prior process was very time consuming and required the attention and care of skilled workmen for its successful completion.

SUMMARY OF THE INVENTION

The invention provides a new method and new apparatus for forming concentric linings of refractory material within the interior of coreless furnaces in substantially reduced time and without the use of skilled workmen, and results in refractory furnace linings of substantially improved quality.

In the method of the invention, a lining form is provided having walls with dimensions that provide a uniform space between the exterior of the lining form and the interior of the furnace and a carrier is provided for the lining form. The carrier provides a lifting structure for the lining form and is adapted for concentric attachment on top of the lining form. The carrier structure further includes means for fastening the carrier to the top of the lining form and means for engaging the furnace and for locating the lining form concentrically within the interior of the furnace. A preferred carrier structure can still further include an upper surface that slopes downwardly from adjacent its center to a peripheral edge, adjacent the top of the lining form, with the peripheral edge having a diameter substantially equal to the outside diameter of the top of the lining form. In the method, the carrier is concentrically attached on the top of the lining form, so the lining form can be carried and lowered into the interior of the furnace, for example, by an overhead crane, while engaging the engagement and locating means of the carrier with alignment means provided on the furnace, thereby concentrically locating the lining form within the furnace, and providing a uniform space therebetween. A preferred method of the invention further includes pouring particulate refractory material onto a downwardly sloping upper surface of the carrier, from which the particulate refractory material is directed into the space between the lining form and the furnace, thereby eliminating the constraint on the size of the bags of refractory material containers that existed in the prior art. Through the use of the method of the invention, the time required to complete the replacement of the refractory lining is substantially reduced, and the need for trained and skilled workmen is substantially reduced.

The invention thus includes a carrier for a lining form that is adopted to form with the interior of the furnace a refractory lining of uniform thickness at the furnace walls. A preferred carrier of the invention comprises a lifting structure whose lower surface engages and concentrically locates the carrier on the lining form. The lifting structure and the lining form have complementary and mating means for fastening the carrier to the lining form, and the lifting structure includes engagement and locating means for locating the carrier and the lining form, when attached, concentrically within the interior of the furnace. The engagement and locating means can comprise, for example, a pair of guides installed in alignment holes in the furnace and a pair of guide bushings carried by the lifting structure so that placement of the lining form within the furnace with the guide bushings of the carrier engaged with the guides installed on the furnace concentrically spaces the walls of the lining form from the furnace walls. A preferred carrier includes an upper surface that slopes downwardly from adjacent its center to a peripheral edge that has a diameter substantially equal to the diameter of the lining form so that particulate material poured onto the upper surface of the carrier falls into the uniform space between the lining form and the furnace.

In the method of the invention, after the space between the lining form and furnace has been filled with refractory material and the carrier has been removed from the top of the lining form, a fixture is attached between the lining form and the furnace that maintains the lining form substantially concentric within the furnace as the refractory material is compacted by vibration.

A preferred fixture for retaining the lining form substantially concentric within the furnace during compaction of the refractory material includes a locking means for installation in alignment holes formed in the furnace, a holding bar adapted for fastening to attachment means provided inside the top of the lining form, and a main bar carrying engagement and holding means for engaging the locking means of the furnace when installed on the furnace, and further carrying clamping mechanisms for clamping the main bar to the holding bar, thereby interconnecting the holding bar with the furnace so the holding bar and the main bar cooperate to maintain the lining form concentric within the furnace wall.

Other features and advantages of the invention will be apparent to those skilled in the art from the more detailed description and the drawings that follow.

BRIEF DESCRIPTION OF THE DRAWINGS

FIG. 1 is a side elevational view of a lining form for use in providing a coreless furnace with a new layer of refractory material;

FIG. 2 is a side elevational view of one embodiment of a carrier of the invention for carrying the lining form of FIG. 1 and aligning the lining form concentrically within the coreless furnace so a uniform layer of refractory material can be provided within the coreless furnace;

DESCRIPTION OF THE BEST MODE OF THE INVENTION

Figure 3:
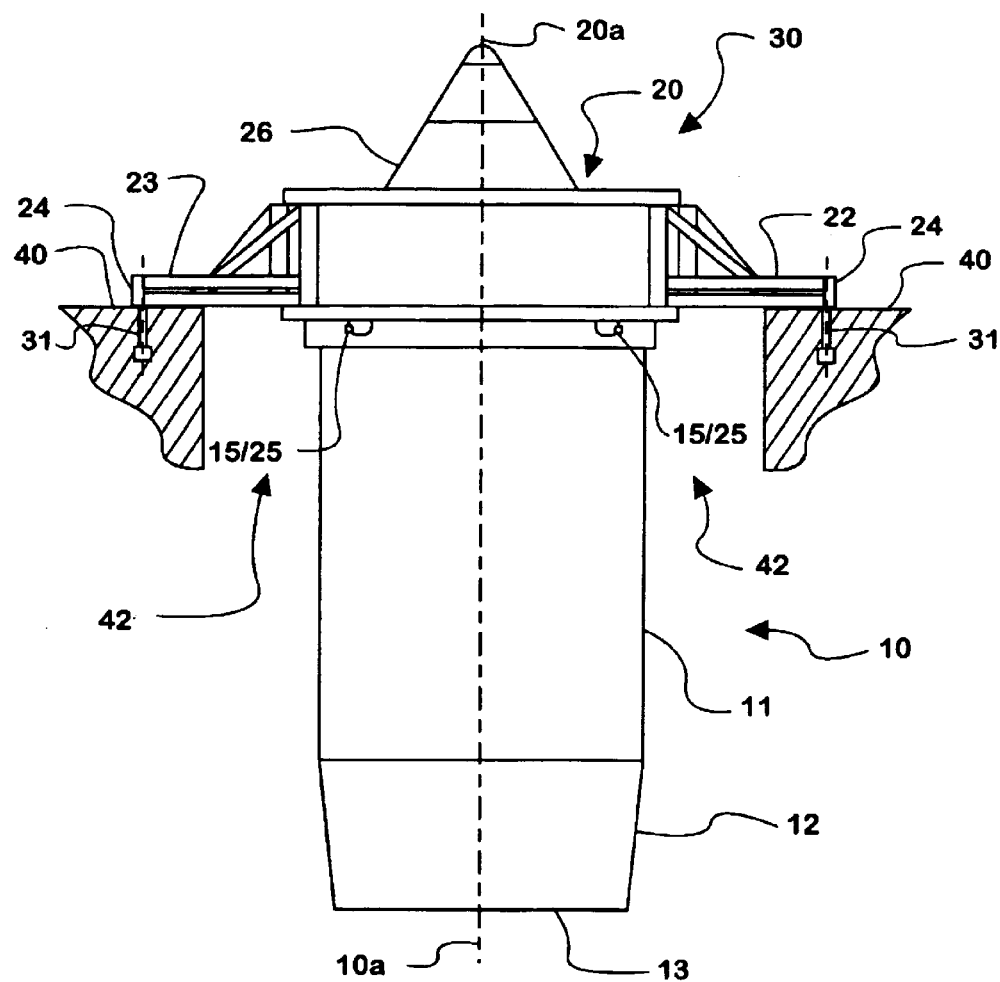
FIG. 3 is a side elevational view of the carrier of FIG. 2, assembled with the lining form of FIG. 1 to provide a carrier-liner assembly.

The invention will be described with reference to the currently known preferred embodiments and steps illustrated through FIGS. 1–8, which are intended to exemplify but not limit the invention. The preferred embodiments and steps of the invention are described for the use with a coreless furnace having cylindrical side walls, although the invention may be used with furnaces having different forms.

FIG. 1 is a side elevational view of a lining form 10 of the type that has been used in the past to provide the uniform replacement of refractory liners adjacent the interior walls of a coreless furnace. As illustrated in FIG. 1, the lining form 10 has a cylindrical sidewall 11 with a tapered lower portion 12 and a closed bottom 13, all of which are dimensioned so that the lining form 10, when properly positioned within the furnace for which it is designed, provides a uniform space between the outer surface of its walls 11, 12, 13, and the interior walls of the furnace in which a replacement refractory lining is to be added. The lining form 10 further comprises an angle iron ring 17 attached to its interior below the open top, preferably for example about 6 inches below the open top, and a plurality of staples 15 to provide fastening means.

Figure 4:
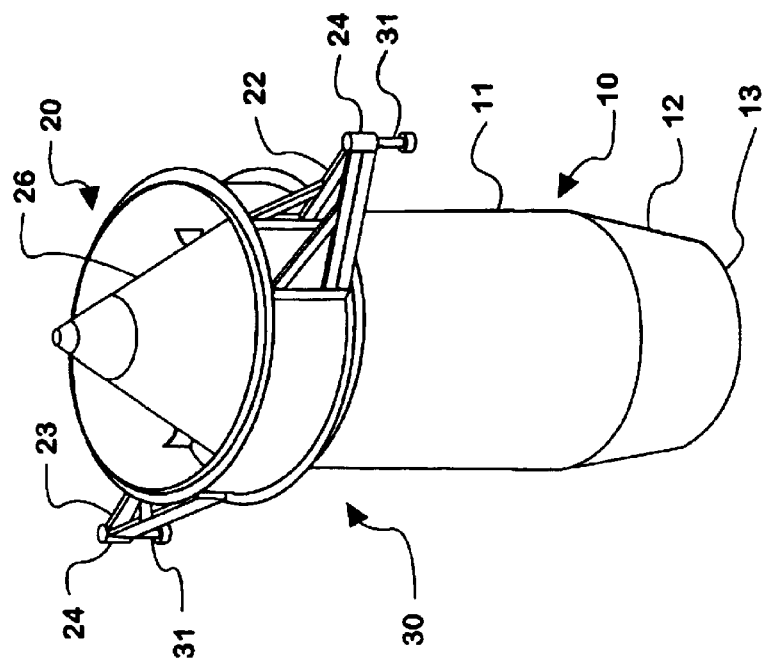
FIG. 4 is a perspective view of the carrier-liner assembly of FIG. 3 comprising the lining form of FIG. 1 and the carrier of FIG. 2.

FIG. 2 is a side elevational view of a carrier 20 to be attached to the lining form 10 of FIG. 1 so that it can be lifted and carried by an overhead crane, lowered within the open top of the coreless furnace to which the refractory material is to be added, and maintained in a position within the coreless furnace to provide a uniform space between the walls 11, 12, 13 of the lining form 10 and the interior walls of the coreless furnace. The carrier 20 includes a collar 28 with an interior diameter adapted for engagement with the top of the lining form 10 and functions to align the central axis 11a of the cylindrical lining form 10 with the central axis of the cylindrical furnace so that the central axes are substantially coaxial and the lining form is concentrically located within the furnace. The collar 28 further provides a plurality of guide bushings 27 adapted to a plurality of pins 25. The guide bushings 27 are adapted for positioning pins 25 for engagement with staples 15 of the lining form. As illustrated in FIG. 2, a preferred carrier 20 comprises a lifting structure 21 adapted for attachment to the lining form 10 (as illustrated in FIGS. 3 and 4). The structure 21 comprises a collar 28 adapted to engage the upper surface of lining form 10 so its central axis 20a is substantially coaxial with the central axis 10a of lining form 10, and further comprises structural elements 22, 23, extending outwardly and terminating in a pair of guide bushings 24, located equally distant from the central axis 20a of the carrier 20. As will be described in greater detail below with respect to FIGS. 3–6, the guide bushings 24 are adapted for engagement with a pair of guide rods 31 installed in existing furnace alignment holes. As indicated, the carrier comprises a plurality of fastening means 25 adapted to cooperate with a plurality of fastening means 15 (shown in FIG. 1) provided on the upper surface of the lining form 10. The fastening means 25 on the carrier 20 and 15 on the lining form 10 comprise complementary mating means for fastening the carrier 20 to the lining form 10. The complementary fastening means 25 and 15 can comprise any of many conventional complementary fastening means, such as screws and threaded openings, but preferably such complementary fastening means comprise pins 25 at the bottom of the collar 28 of structural means 21 to provide the fastening means 25 and staples added to the upper surface of the lining form 10 to provide the fastening means 15, the complementary fastening means 15/25 being located so that when the carrier 20 is placed on top of the lining form 10, the pins 25 may be inserted through openings in the complementary staples 15 to securely fasten the carrier 20 on the top of the lining form 10 with the central axis 20a coaxially aligned with the central axis 10a of the lining form, as illustrated in FIGS. 3 and 4.

The carrier 20 also preferably comprises a conical upper surface 26 that extends from the central axis 20a of the carrier at its upper end to the bottom portion 20b of the carrier 20. The outer diameter of the bottom peripheral edge of the conical surface 26 is preferably substantially equal to the outer diameter of the upper end of the lining form 10. In the preferred embodiment, the collar 28 is attached to the peripheral edge of the conical surface 26. As will be described further below, the conical surface 26 can direct particulate refractory material poured on its outer surface so that substantially the entire quantity of the particulate refractory material poured on the outer surface 26 will flow under the influence of gravity into the space around the lining form 10 with an insubstantial amount falling within the lining form 10. Accordingly, while it is preferred that the lower peripheral edge of the conical surface 26 have an outer diameter at least equal to the outer diameter of the open top of the lining form 10, it may be somewhat smaller than the outside diameter of the lining form 10 as the momentum imparted particulate material flowing down the sides of the conical form 26 can carry the particulate material beyond the open top of the lining form 10. While a conical upper surface 26 is shown, the upper surface may have any shape that slopes downwardly between adjacent its center and its peripheral edge so that particulate material poured onto it will be conveyed to and off of the peripheral edge.

FIG. 3 is a side elevational view of the carrier 20 fastened to the lining form 10 by engagement of the fastening means 15/25 to provide a carrier-liner assembly 30. FIGS. 3 and 4 also illustrates a pair of guide rods 31 that are carried by a pair of alignment holes in the furnace 40 in which the carrier-liner assembly 30 is to be placed.

Figure 5:
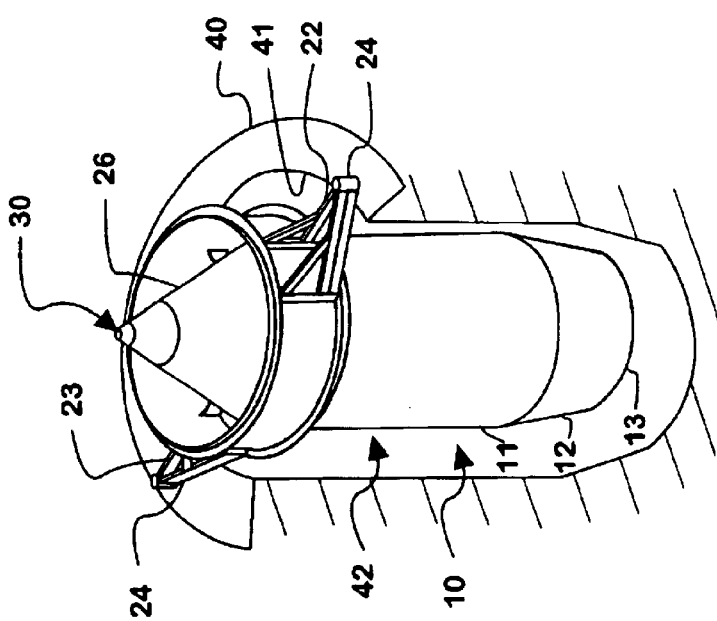
FIG. 5 is a perspective view of the carrier-liner assembly of FIGS. 3 and 4, positioned concentrically within a linerless furnace, which is partially broken away, to more fully illustrate the carrier-liner assembly of FIGS. 3 and 4 in position to form a uniform space between the lining form of FIG. 1 and the interior surface of the furnace.

In the method of this invention, after the carrier 20 has been fastened on top of the lining form 10, an overhead crane is connected with the structure 21 at any location conveniently provided on the structure 21, and the carrier-liner assembly 30 is lifted and lowered into a furnace from which a worn refractory liner has been removed, while the guide bushings 24 are aligned with and placed over the guide rods 31, to thereby align the lining form assembly 10 concentrically within the furnace 40, as illustrated in FIG. 5. The engagement of the guide bushings 24 with the guide rods 31 ensures that the central axes 10a, 20a of the carrier-liner assembly 30 lie substantially coaxially with the central axis of the cylindrical inner wall 41 of the furnace 40, providing a uniform space 42 between the inner wall 41 of the furnace 40 and the outer walls 11, 12, 13 of the lining form 10.

Figure 7:
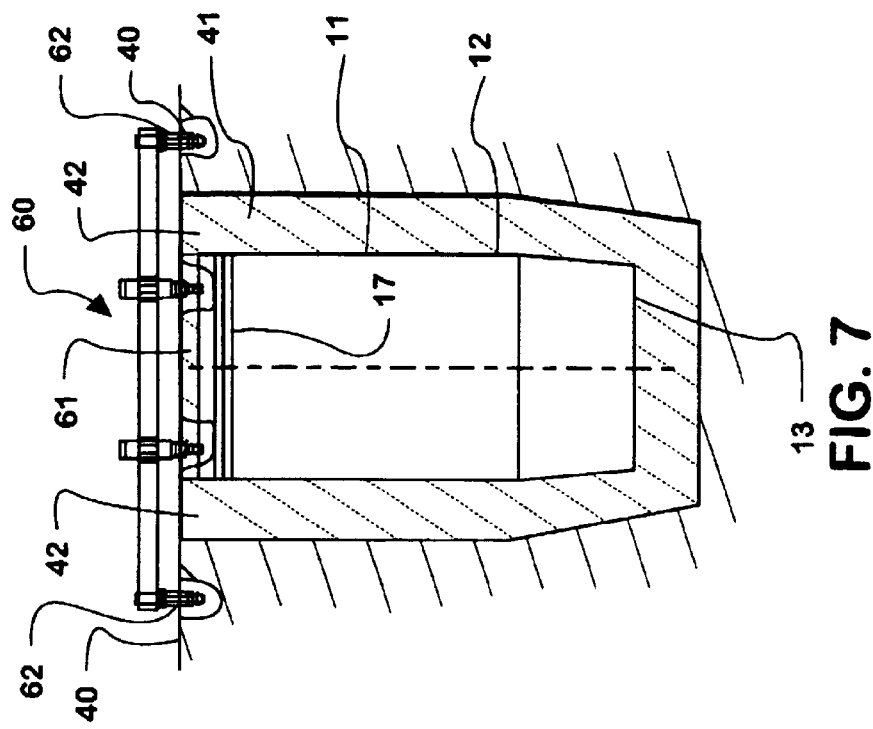
FIG. 7 is a cross-sectional view of a furnace and a lining form with the space therebetween filled with refractory material and illustrating a fixture of the invention for retaining the lining form concentric within the furnace as particulate refractory material is vibrated for compaction.
Figure 6:
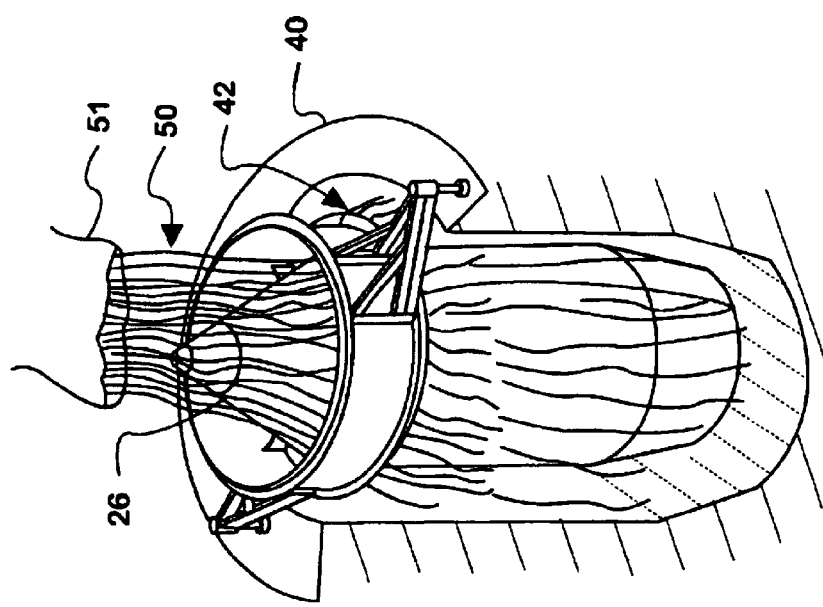
FIG. 6 is a perspective view corresponding to FIG. 5, showing a refractory material being added to the space between the lining form and the interior furnace wall, by pouring particular refractory material onto the upper surface of the carrier.

With the carrier-liner assembly 30 positioned within the furnace 40, the overhead crane, or other means, can be used to pour the particulate refractory material 50 from bags 51 of any size onto the conical surface 26, which directs the falling particulate matter 50 into the space 42, where it collects to form a refractory liner for the furnace 40. Refractory material 50 is poured into the space 42 until it is full of the refractory material 50, as illustrated in FIG. 7. After the space 42 is completely full of the refractory material 50, the carrier 20 is disconnected from the lining form 10 by disengagement of the fastening means 15/25, and the carrier 20 is lifted from the guide rods 31 and the lining form 10.

The formation of a satisfactory refractory liner for the furnace 40 requires that the particulate refractory material 50 within the space 42 be compacted, and such compaction of the refractory material 50 generally requires vibration of the refractory material 50 to compact it within the space 42, and is effected by attaching a vibrator to the lining form 10. During compaction of the refractory material 50, the lining form 10 must be maintained in its position concentrically located within the inner walls 41 of the furnace 40 in order that the refractory liner being formed will have a uniform thickness. In the invention, a fixture 60 is provided structurally interconnecting the lining form 10 with the furnace 40 to hold the lining form 10 concentric within the furnace 40, thereby maintaining the uniformity of the space 42 and the thickness of the resulting refractory liner as a refractory material 50 is formed into a compacted mass.

Figure 8:
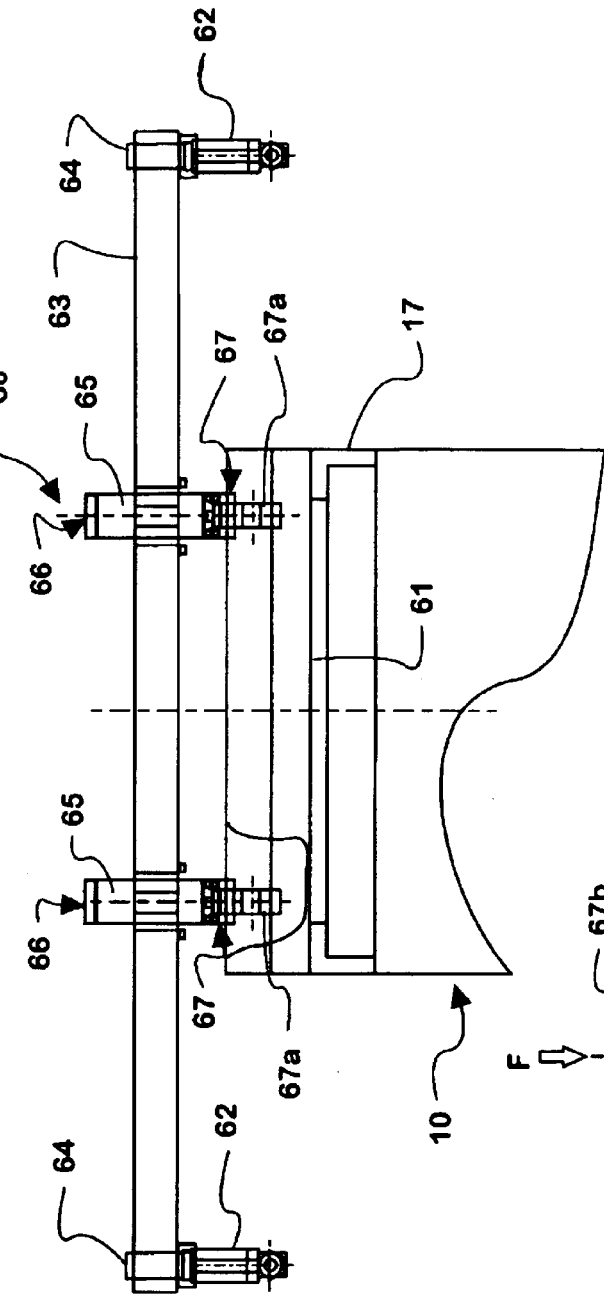
FIG. 8 is an elevational view of the fixture of FIG. 7 to better illustrate its components.
Figure 8A:
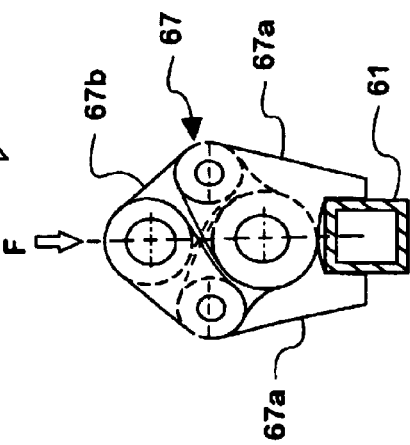
FIG. 8A is a side elevational view of one of the means of FIG. 8 used to hold the lining form concentric within the furnace as particulate refractory material is compacted.

The structure and action of the fixture 60 will be described with respect to FIGS. 7, 8 and 8A. As illustrated in FIGS. 7 and 8, a holding bar 61 made from a rigid material, such as square steel tubing, is attached to an angle iron ring 17 (or other such attachment means), located inside the upper end of the lining form 10, by for example, screws or bolts. A pair of locking means 62 are temporarily installed in the furnace alignment holes, which had previously carried the guide rods 31. A main bar 63, also made of rigid material, such as square steel tubing, is placed on and engaged with the locking means 62 and is positioned thereby over the holding bar 61. The main bar 63 is then rigidly connected to the locking means 62, for example, by a pair of sliding brackets 64. The main bar 63 also carries a pair of clamping mechanisms 65, such as pressure-operated piston/cylinder units, that are pneumatically operated and drive self-clamping jaws 67 downwardly until they engage and grip holding bar 61. As shown in FIG. 8A, each of the self-clamping jaws 67 comprise a plurality of gripping elements 67a pivotally carried by a drive element 67b attached to and driven by a piston of a piston/cylinder unit 65. As schematically indicated in FIG. 8A, as motion of the self-clamping jaws 67 stop, as the self-clamping jaws 67 meet the holding bar 61, the force F applied to drive element 67b urges the gripping elements 67a downwardly and inwardly to grip the holding bar 61. Each of the clamping mechanisms 65 carries a quick disconnect 66 for connection with a compressed air hose. Once the main bar 63 is rigidly fastened to the furnace by means of the locking mechanisms 62, compressed air is connected to the clamping mechanisms 65 and the compressed air drives self-clamping jaws 67 downwardly until they engage and grip the holding bar 61, and as a result of the rigid interconnection between the lining form 10 and the furnace by means of the main bar 63, the clamping mechanisms 65, 67, locking mechanisms 62 and holding bar 61, lining form 10 can be held substantially concentric within the furnace 40 as the refractory material 50 is compacted within the space 42 by vibration.

When compaction of the refractory material is completed, the fixture 60 is removed from the lining form 10, and formation of the refractory lining within the furnace 40 is completed by heating the lining form 10 from within, in a manner well known in the art, providing the furnace with a completed and uniformly thick layer of refractory material 50 adjacent its interior walls.

The invention thus comprises a method for forming a uniform lining of refractory material within the interior of a coreless furnace by providing a lining form having walls dimensioned to provide a uniform space between the walls of the lining form and the interior of the furnace, providing a carrier for the lining form having a structure adapted for a concentric location and attachment on top of the lining form, said carrier having furnace engagement and locating means for engaging the carrier with the furnace and locating the lining form, when attached, concentrically within the interior of the furnace, attaching the carrier concentrically on top of the lining form, and connecting the carrier to the lining form to provide a carrier-liner assembly, and lowering the carrier-liner assembly into the interior of the furnace while engaging the furnace engagement and locating means of the carrier with the furnace to concentrically locate the lining form within the furnace and provide a uniform space therebetween. In a preferred method of the invention, the carrier is provided with an upper surface that slopes downwardly from adjacent its center to its peripheral edge, for example a conical upper surface, and particulate refractory material is poured into the downwardly sloping upper surface, which conveys the particulate refractory material into the space between the lining form and the furnace. For example, by pouring particulate refractory material onto a conical upper surface of the carrier as described above, the particulate refractory material can be directed substantially entirely into the uniform space between the form and the furnace.

The method of the invention further includes providing a fixture, while vibrating the granular refractory material to compact it within the space between the lining form and the furnace, and thereby holding the lining form concentric with respect to the furnace. In such a method, for example, by fastening a holding bar within the lining form at its top, and fastening a main bar having clamping means for cooperating with the holding bar, and further having engagement and holding means for engaging the furnace and thereby holding the lining form substantially concentric with respect to the furnace.

As noted above, a carrier is provided by the invention for a lining form which is adapted to form, with the interior of a coreless furnace, a refractory lining of uniform thickness at the interior of the furnace walls. Such a carrier comprises a structure that can be concentrically positioned at the open top of the lining form and permit lifting of a lining form. The carrier includes fastening means for cooperating with complementary fastening means at the upper end of the lining form for connecting the carrier and lining form into the carrier-liner assembly. The carrier structure also provides a pair of engagement and locating means, for locating the carrier-liner assembly concentrically within the interior of the furnace. Placement of the carrier-liner assembly within the furnace with its engagement and locating means engaged with a pair of guides installed in alignment holes formed in the furnace concentrically locates the lining form within the furnace to form a uniform space between the outer surface of the lining form and interior walls of the furnace. The carrier can further have an upper surface that slopes downwardly from adjacent its center to a peripheral edge, having an outside diameter substantially equal to the outside diameter of the liner, so that refractory material poured onto the upper surface of the carrier falls into the uniform concentric space between the lining form and the furnace.

It is also noted above the invention includes the use of a fixture for retaining the lining form concentric within the furnace while the refractory material is being compacted by vibration. Such a fixture comprises locking means for installation in alignment holes formed in the furnace, a holding bar adapted for fastening to an attachment means formed inside the top of the lining form, and a main bar carrying engagement means for engaging, when installed on the furnace, the locking means of the furnace, and further carrying means for engaging and gripping the holding bar for clamping the main bar to the holding bar, thereby connecting the main bar and the holding bar together so that the holding bar and main bar cooperate to maintain the lining form concentric within the furnace.

As a result of the invention, the time required to install a replacement refractory lining within a coreless furnace is substantially reduced to nearly a theoretical minimum, the need for the use of skilled workmen for the process is substantially eliminated, the process of compacting the refractory material is substantially more reliable and does not require the use of skilled workmen, and the quality of the resulting furnace lining is substantially improved.

The foregoing description and drawing should be regarded as illustrative rather than limiting, and it should be understood that it is the following claims, including all equivalents, that are intended to define the spirit and scope of this invention.

What is claimed is:

1. A method for forming a uniform lining of refractory material within the interior of a coreless furnace, comprising providing a lining form having walls dimensioned to provide a uniform space between the liner walls and the interior of the furnace;

providing a carrier for the lining form, said carrier having a structure adapted for concentric location and attachment on top of a lining form, and for carrying the lining form when attached thereto, said carrier further having furnace engagement and locating means for engaging said furnace and locating said lining form, when attached, concentrically within the interior of the furnace, and further having a conical upper surface having an outer diameter substantially equal to the diameter of the lining form;

attaching the carrier concentrically on top of the lining form;

lowering at least part of the lining form into the interior of the furnace while engaging the furnace engagement and locating means of the carrier with said furnace, thereby concentrically locating said lining form within said furnace, and pouring particulate refractory material onto said conical upper surface, whereby the particulate refractory material is directed into the uniform space between the lining form and the furnace.

2. The method of claim 1 wherein the particulate refractory material is vibrated for compaction within the space between the lining form and the furnace.

3. The method of claim 2 wherein a fixture is provided interconnecting the lining form and the furnace during vibration of the particulate refractory material to maintain the lining form concentric with respect to the furnace.

4. The method of claim 3 wherein said fixture is provided by providing a holding bar adapted to be fastened to the lining form, fastening the holding bar within the lining form at its top, and providing a main bar adapted to be connected between the holding bar and the furnace, said main bar having clamping mechanisms for cooperating with the holding bar, and further having engagement and holding means for engaging the furnace, and attaching the engagement and holding means of the main bar to the furnace and the clamping mechanisms of the main bar to the holding bar, thereby holding the lining form concentric with respect to the furnace during vibration of the refractory material.

5. A carrier adapted for the formation of a refractory lining of uniform thickness on the interior of a furnace, with the use of a lining form having a cylindrical side wall and a closed bottom and providing, when concentrically supported within the furnace, a uniform space between its exterior surface and the interior surface of the furnace, said carrier comprising:

a lifting structure adapted for concentric location on and attachment to the top of the lining form and having engaging and locating means adapted for engagement with the furnace and for location of the lining form, when attached, concentrically within the furnace, said carrier further having a conical upper surface with the outside diameter of its lowest edge being substantially equal to the outside diameter of the lining form, said lining form and carrier having complementary mating means for fastening said carrier to said lining form, wherein the placement of at least part of said lining form within said furnace with said engaging and locating means of the carrier engaged with the furnace locates said lining form concentrically within the furnace to provide a uniform space between the lining form and the surface, and wherein particulate refractory material poured onto the conical upper surface is directed into the concentric space.

6. The carrier of claim 5 wherein the engaging and locating means of the carrier comprise a pair of guide bushings adapted for engagement with a pair of guides installed in alignment holes formed in the furnace.

7. A fixture for retaining a lining form concentric within the furnace during compaction of refractory materials, comprising a pair of locking means for installation in a pair of alignment holes formed in the furnace, a holding bar adapted to be fastened to attachment means formed inside the top of the lining form, and a main bar carrying engagement and holding means for engaging the locking means of the furnace when installed on the furnace, and locking mechanisms for clamping to the holding bar, whereby the main bar and the holding bar, when connected together and to the furnace, provide a rigid structure to hold the lining form concentric within the furnace.

8. The fixture of claim 7 wherein said locking mechanisms comprise a plurality of pressure-actuated piston/cylinder units carried by said main bar, the pistons of each of said piston/cylinder units carrying a set of self-clamping jaws adapted to engage and grip the holding bar as the piston is driven by pressure applied to cylinders of the piston/cylinder units.

9. A method for forming a uniform lining of refractory material within the interior of a coreless furnace, comprising:

providing a lining form having walls dimensioned to provide a uniform space between the liner walls and the interior of the furnace;

providing a carrier for the lining form, said carrier having a structure adapted for concentric location and attachment on top of a lining form, and for carrying the lining form when attached thereto, said carrier further having furnace engagement and locating means for engaging said furnace and locating said lining form, when attached, concentrically within the interior of the furnace;

attaching the carrier concentrically on top of the lining form; and lowering at least part of the lining form into the interior of the furnace while engaging the furnace engagement and locating means of the carrier with said furnace, thereby concentrically locating said lining form within said furnace, and providing a uniform space therebetween.

10. The method of claim 9 wherein the carrier has an upper surface shaped to slope downwardly from its center to its peripheral edge, and particulate refractory material is poured on the upper surface and conveyed thereby into the uniform space between the lining form and furnace.

11. The method of claim 10 wherein the upper surface is a cone having a peripheral edge adjacent the top of the lining form with a diameter substantially equal to the diameter of the lining form.

12. A carrier for a lining form adapted to form a refractory lining of uniform thickness at the interior furnace walls, with the use of a lining form having a cylindrical side wall and a closed bottom and providing, when concentrically supported within a furnace, a uniform space between its exterior surface and the interior surface of the furnace, said carrier comprising a lifting structure adapted for concentric location on and attachment to the top of the lining form and having engaging and locating means adapted for engagement with the furnace and for location of the lining form, when attached, concentrically within the furnace, said lining form and carrier having complementary mating means for fastening said carrier to said lining form, wherein the placement of at least part of said lining form within said furnace with said engaging and locating means of the carrier engaged with the furnace locates said lining form concentrically within the furnace to provide a uniform space between the lining form and the surface.

13. The carrier of claim 12 wherein the engaging and locating means of the carrier comprise a pair of guide bushings adapted for engagement with a pair of guides installed in alignment holes formed in the furnace.

14. The carrier of claim 12 further comprising an upper surface shaped to slope downwardly from adjacent its center to its peripheral edge, said peripheral edge lying closely adjacent the upper end of the lining form, when attached to the carrier.

15. The carrier of claim 12 wherein the carrier is adapted for concentric location on and attachment to the top of the lining form by a collar at its bottom with an inside diameter adapted to concentrically engage the top of the lining form, said complementary mating means comprising a plurality of guides on said collar for guiding a plurality of pins for engagement with a plurality of staples on top of the lining form.

16. A method comprising the steps of:

providing a lining form having at least one exterior wall disposable in an interior of a furnace having at least one interior wall;

providing a carrier having a directing surface, aligning means, and a structure attachable to the lining form;

installing at least a part of the lining form into the interior of the furnace while engaging the aligning means with the furnace, thereby creating a substantially uniform space between the at least one exterior wall and the at least one interior wall;

pouring refractory material onto the directing surface that directs the refractory material into the uniform space, yielding a substantially uniform lining in the interior of the furnace.

17. The method of claim 16, further comprising the step of attaching the carrier to the lining form.

18. The method of claim 16, wherein the carrier is provided with the capability of carrying the lining form when the lining form is coupled with the carrier.

* * * * *